(12) United States Patent
Carley et al.

(10) Patent No.: US 7,705,039 B2
(45) Date of Patent: Apr. 27, 2010

(54) METHOD FOR TREATING SLEEP APNEA

(75) Inventors: David W. Carley, Evanston, IL (US); Miodrag Radulovacki, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1329 days.

(21) Appl. No.: 10/472,136

(22) PCT Filed: Apr. 8, 2002

(86) PCT No.: PCT/US02/10876

§ 371 (c)(1),
(2), (4) Date: Feb. 24, 2004

(87) PCT Pub. No.: WO02/080903

PCT Pub. Date: Oct. 17, 2002

(65) Prior Publication Data

US 2004/0127572 A1 Jul. 1, 2004

Related U.S. Application Data

(60) Provisional application No. 60/281,949, filed on Apr. 6, 2001.

(51) Int. Cl.
*A61K 31/352* (2006.01)
*A61K 31/164* (2006.01)

(52) U.S. Cl. ....................................... 514/455; 514/627
(58) Field of Classification Search ........................ None
See application file for complete search history.

(56) References Cited

U.S. PATENT DOCUMENTS

| 6,096,740 | A | 8/2000 | Mechoulam et al. |
| 6,211,230 | B1 | 4/2001 | Filbert et al. |

FOREIGN PATENT DOCUMENTS

| EP | 0 053 754 | 6/1982 |
| EP | 0 125 634 | 11/1984 |

OTHER PUBLICATIONS

The Merck Index, 17$^{th}$ edition (1999), pp. 1415-1416.*
Hanna et al., Aviation Space and Environmental Medicine, 47(6), (Jun. 1976) 634-9.*
Zwilich et al., J.Clin. Investigation (Jun. 1982) 69(6): 1286-92.*
Bradley et al., Medical Clinics of North America, (1985), 69(6), pp. 1169-1185.*
Sqto et al., Circulation, 96(1), (Jul. 1, 1997), pp. 274-281.*

* cited by examiner

*Primary Examiner*—Phyllis G. Spivack
(74) *Attorney, Agent, or Firm*—Marshall, Gerstein & Borun LLP (57) ABSTRACT

A method of ameliorating a sleep-related breathing disorder via administration of at least one cannabimimetic agent, such as oleamide or $\Delta^9$THC, to an individual in need of treatment.

4 Claims, 7 Drawing Sheets

METHOD FOR TREATING SLEEP APNEA

CROSS-REFERENCE TO RELATED APPLICATIONS

This is the U.S. national phase application of International Application No. PCT/US02/10876, filed Apr. 8, 2002, which claims the benefit of U.S. provisional patent application Ser. No. 60/281,949, filed Apr. 6, 2001.

BACKGROUND OF THE INVENTION

1. Field of the Invention

This invention generally relates to methods for the pharmacological treatment of breathing disorders and, more specifically, to the administration of agents or combinations of agents having cannabimimetic activity for the alleviation of sleep apnea (central and obstructive) and other sleep-related breathing disorders.

2. Related Technology

Over the past several years much effort has been devoted to the study of a discrete group of breathing disorders that occur primarily during sleep with consequences that may persist throughout the waking hours in the form of sleepiness, thereby manifesting itself into substantial economic loss (e.g., thousands of lost man-hours) or employment safety factors (e.g., employee non-attentiveness during operation of heavy-machinery). Sleep-related breathing disorders are characterized by repetitive reduction in breathing (hypopnea), periodic cessation of breathing (apnea), or a continuous or sustained reduction in ventilation.

In general sleep apnea is defined as an intermittent cessation of airflow at the nose and mouth during sleep. By convention, apneas of at least 10 seconds in duration have been considered important, but in most individuals the apneas are 20-30 seconds in duration and may be as long as 2-3 minutes. While there is some uncertainty as to the minimum number of apneas that should be considered clinically important, by the time most individuals come to attention of the medical community they have at least 10 to 15 events per hour of sleep.

Sleep apneas have been classified into three types: central, obstructive, and mixed. In central sleep apnea the neural drive to all respiratory muscles is transiently abolished. In obstructive sleep apneas, airflow ceases despite continuing respiratory drive because of occlusion of the oropharyngeal airway. Mixed apneas, which consist of a central apnea followed by an obstructive component, are a variant of obstructive sleep apnea. The most common type of apnea is obstructive sleep apnea.

Obstructive sleep apnea syndrome (OSAS) has been identified in as many as 24% of working adult men and 9% of similar women, with peak prevalence in the sixth decade. Habitual heavy snoring, which is an almost invariant feature of OSAS, has been described in up to 24% of middle aged men, and 14% of similarly aged women, with even greater prevalence in older subjects.

Obstructive sleep apnea syndrome's definitive event is the occlusion of the upper airway, frequently at the level of the oropharynx. The resultant apnea generally leads to a progressive-type asphyxia until the individual is briefly aroused from the sleeping state, thereby restoring airway patency and thus restoring airflow.

An important factor that leads to the collapse of the upper airway in OSAS is the generation of a critical subatmospheric pressure during the act of inspiration that exceeds the ability of the airway dilator and abductor muscles to maintain airway stability. Sleep plays a crucial role by reducing the activity of the muscles of the upper airways including the dilator and abductor muscles.

In most individuals with OSAS the patency of the airway is also compromised structurally and is therefore predisposed to occlusion. In a minority of individuals the structural compromise is usually due to obvious anatomic abnormalities, i.e, adenotonsillar hypertrophy, retrognathia, or macroglossia. However, in the majority of individuals predisposed to OSAS, the structural abnormality is simply a subtle reduction in airway size, i.e., "pharyngeal crowding." Obesity also frequently contributes to the reduction in size seen in the upper airways. The act of snoring, which is actually a high-frequency vibration of the palatal and pharyngeal soft tissues that results from the decrease in the size of the upper airway lumen, usually aggravates the narrowing via the production of edema in the soft tissues.

The recurrent episodes of nocturnal asphyxia and of arousal from sleep that characterize OSAS lead to a series of secondary physiologic events, which in turn give rise to the clinical complications of the syndrome. The most common manifestations are neuropsychiatric and behavioral disturbances that are thought to arise from the fragmentation of sleep and loss of slow-wave sleep induced by the recurrent arousal responses. Nocturnal cerebral hypoxia also may play an important role. The most pervasive manifestation is excessive daytime sleepiness. OSAS is now recognized as a leading cause of daytime sleepiness and has been implicated as an important risk factor for such problems as motor vehicle accidents. Other related symptoms include intellectual impairment, memory loss, personality disturbances, and impotence.

The other major manifestations are cardiorespiratory in nature and are thought to arise from the recurrent episodes of nocturnal asphyxia. Most individuals demonstrate a cyclical slowing of the heart during the apneas to 30 to 50 beats per minute, followed by tachycardia of 90 to 120 beats per minute during the ventilatory phase. A small number of individuals develop severe bardycardia with asystoles of 8 to 12 seconds in duration or dangerous tachyarrhythmias, including unsustained ventricular tachycardia. OSAS also aggravates left ventricular failure in patients with underlying heart disease. This complication is most likely due to the combined effects of increased left ventricular afterload during each obstructive event, secondary to increased negative intrathoracic pressure, recurrent nocturnal hypoxemia, and chronically elevated sympathoadrenal activity.

Central sleep apnea is less prevalent as a syndrome than OSAS, but can be identified in a wide spectrum of patients with medical, neurological, and/or neuromuscular disorders associated with diurnal alveolar hypoventilation or periodic breathing. The definitive event in central sleep apnea is transient abolition of central drive to the ventilatory muscles. The resulting apnea leads to a primary sequence of events similar to those of OSAS. Several underlying mechanisms can result in cessation of respiratory drive during sleep. First are defects in the metabolic respiratory control system and respiratory neuromuscular apparatus. Other central sleep apnea disorders arise from transient instabilities in an otherwise intact respiratory control system.

Many healthy individuals demonstrate a small number of central apneas during sleep, particularly at sleep onset and in REM sleep. These apneas are not associated with any physiological or clinical disturbance. In individuals with clinically significant central sleep apnea, the primary sequence of events that characterize the disorder leads to prominent physiological and clinical consequences. In those individuals with central sleep apnea alveolar hypoventilation syndrome, daytime hypercapnia and hypoxemia are usually evident and the clinical picture is dominated by a history of recurrent respiratory failure, polycythemia, pulmonary hypertension, and right-sided heart failure. Complaints of sleeping poorly, morning headache, and daytime fatigue and sleepiness are also prominent. In contrast, in individuals whose central sleep apnea results from an instability in respiratory drive, the clinical picture is dominated by features related to sleep disturbance, including recurrent nocturnal awakenings, morning fatigue, and daytime sleepiness.

Currently, the most common and most effective treatment, for adults with sleep apnea and other sleep-related breathing disorders are mechanical forms of therapy that deliver positive airway pressure (PAP). Under PAP treatment, an individual wears a tight-fitting plastic mask over the nose when sleeping. The mask is attached to a compressor, which forces air into the nose creating a positive pressure within the patient's airways. The principle of the method is that pressurizing the airways provides a mechanical "splinting" action, which prevents airway collapse and therefore, obstructive sleep apnea. Although an effective therapeutic response is observed in most patients who undergo PAP treatment, many patients cannot tolerate the apparatus or pressure and refuse treatment. Moreover, recent covert monitoring studies clearly demonstrate that long-term compliance with PAP treatment is very poor.

A variety of upper airway and craniofacial surgical procedures have been attempted for treatment of OSAS. Adenotonsillectomy appears to be an effective cure for OSAS in many children, but upper airway surgery is rarely curative in adult patients with OSAS. Surgical "success" is generally taken to be a 50% reduction in apnea incidence and there are no useful screening methods to identify the individuals that would benefit from the surgery versus those who would not derive a benefit.

Pharmacological treatments of several types have been attempted in patients with sleep apnea but, thus far, none have proven to be generally useful. A recent systematic review of these attempts is provided by Hudgel [*J. Lab. Clin. Med.*, 126:13-18 (1995)]. A number of compounds have been tested because of their expected respiratory stimulant properties. These include (1) acetazolamide, a carbonic anhydrase inhibitor that produced variable improvement in individuals with primary central apneas but caused an increase in obstructive apneas, (2) medroxyprogesterone, a progestin that has demonstrated no consistent benefit in OSAS, and (3) theophylline, a compound usually used for the treatment of asthma, which may benefit patients with central apnea but appears to be of no use in adult patients with obstructive apnea.

Other attempted pharmacological treatment includes the administration of adenosine, adenosine analogs and adenosine reuptake inhibitors (U.S. Pat. No. 5,075,290). Specifically, adenosine, which is a ubiquitous compound within the body and which levels are elevated in individuals with OSAS, has been shown to stimulate respiration and is somewhat effective in reducing apnea in an animal model of sleep apnea.

Other possible pharmacological treatment options for OSAS include agents that stimulate the brain activity or are opioid antagonists. Specifically, since increased cerebral spinal fluid opioid activity has been identified in OSAS, it is a logical conclusion that central stimulants or opioid antagonists would be a helpful treatment of OSAS. In reality, doxapram, which stimulates the central nervous system and carotid body chemoreceptors, was found to decrease the length of apneas but did not alter the average arterial oxygen saturation in individuals with obstructive sleep apnea. The opioid antagonist naloxone, which is known to stimulate ventilation was only slightly helpful in individuals with obstructive sleep apnea.

Because OSAS is strongly correlated with the occurrence of hypertension, agents such as angiotensin-converting enzyme (ACE) inhibitors may be of benefit in treating OSAS individuals with hypertension but this does not appear to be a viable treatment for OSAS itself.

Finally, several agents that act on neurotransmitters and neurotransmitter systems involved in respiration have been tested in individuals with OSAS. Most of these compounds have been developed as anti-depressant medications that work by increasing the activity of monoamine neurotransmitters including norepinephrine, dopamine, and serotonin. Protriptyline, a tricyclic anti-depressant, has been tested in several small trials with variable results and frequent and significant side effects. As serotonin may promote sleep and stimulate respiration, tryptophan, a serotonin precursor and selective serotonin reuptake inhibitors have been tested in individuals with OSAS. While a patent has been issued for the use of the serotonin reuptake inhibitor, fluoxetine (U.S. Pat. No. 5,356,934), initial evidence suggests that these compounds may yield measurable benefits in only approximately 50% of individuals with OSAS. Therefore in view of the fact that the only viable treatment for individuals suffering from sleep-related breathing disorders is a mechanical form of therapy (PAP) for which patient compliance is low, and that hopes for pharmacological treatments have yet to come to fruition, there remains a need for simple pharmacologically-based treatments that would offer benefits to a broad base of individuals suffering from a range of sleep-related breathing disorders. There also remains a need for a viable treatment of sleep-related breathing disorders that would lend itself to a high rate of patient compliance.

SUMMARY OF THE INVENTION

The invention is directed to providing pharmacological treatments for the prevention or amelioration of sleep-related breathing disorders (for example, but not limited to obstructive sleep apnea syndrome, obstructive sleep apnea/hypopnea syndrome, upper airway resistance syndrome, apnea of prematurity, congenital central hypoventilation syndrome, obesity hypoventilation syndrome, central sleep apnea syndrome, Cheyne-Stokes respiration, and snoring).

The present invention is directed to methods for the prevention or amelioration of sleep-breathing disorders the method comprising administering to a patient in need thereof an effective amount of a cannabimimetic agent or a combination of cannabimimetic agents. Such cannabimimetic agents may include (but are not limited to):

(a) CB-1 receptor agonists selected from the group consisting arachidonyl-2'-chloroethylamide, arachidonyl-cyclopropylamide, and methanandamide;

(b) CB-2 receptor agonists selected from the group consisting L-759633, L-759656, JWH-133, HU-308, and palmitoylethanolamide;

(c) non-selective cannabinoid receptor agonists selected from the group consisting of 9-tetrahydrocannabinol, 8-tetrahydrocannabinol, HU-210, CP55940, WIN55, 212-2, O-1057, 2-arachidonoyl glycerol, anandamide, dexanabinol, nabilone, levonantradol, and N-(2-hydroxyethyl)hexadecanoamide; and (d) endocannabinoid selected from the group consisting of oleamide, linoleoylethanolamide, and oleoylethanolamide.

The present invention is also directed to the prevention or amelioration of sleep-related breathing disorder the method comprising administering to a patient in need thereof an effective amount of an agent that inhibits cannabinoid metabolism or a combination of agents that inhibit cannabinoid metabolism. Exemplary agents would include (but are not limited to) phenylmethylsulphonyl fluoride, palmitylsulphonyl fluoride, stearylsulphonyl fluoride, methyl arachidonyl fluorophosphonate, and O-1887.

The present invention is further directed to methods of preventing or ameliorating sleep-related breathing disorder the method comprising administering to a patient in need thereof an effective amount of an agent that inhibits endocannabinoid membrane transport or a combination of agents that inhibit endocannabinoid membrane transport. Such agents would include (but are not limited to) AM404, VDM11, and arvanil.

The present invention is also directed to methods of preventing or ameliorating sleep-related breathing disorder the method comprising administering to a patient in need thereof an effective amount of a cannabimimetic precursor or prodrug or a or a combination of cannabimimetic precursors or prodrugs. Exemplary agents would include (but are not limited to) N-arachidonoylphosphatidylethanolamine and quaternary nitrogen-containing glycinate esters of dexanabinol.

BRIEF DESCRIPTION OF THE DRAWINGS

Overall FIGS. 2A and 2B shows the effect of intraperitoneal oleamide and $\Delta^9$THC on respiratory rate (RR). With respect to FIG. 2A, data is presented as an interaction plot depicting average RR during Wake (left column), NREM sleep (middle column), and REM sleep (right column) following $\Delta^9$THC administration. Concentrations of $\Delta^9$THC are coded by symbol according to the legend. RR was lowest during NREM sleep and was unaffected by time during the recording. RR was significantly reduced in all sleep/wake states after administration of 10.0 mg/kg $\Delta^9$THC.

FIG. 3. sets forth group mean data for the impact of oleamide on sleep architecture. The ordinate displays the percentage of each 6-hour recording scored as Wake (left column), NREM sleep (middle column), or REM sleep (right column). Injection type is coded according to the inset legend. Significant changes in sleep architecture with respect to vehicle were observed as labeled.

DETAILED DESCRIPTION OF THE INVENTION

*Cannabis* produces well recognized behavioral effects and two types of G protein-coupled receptors ($CB_1$ and $CB_2$) have been characterized which bind the active components of *Cannabis* [Shire et al., *Life Sci.*, 65:627-35 (1999)]. Notwithstanding such well-recognized effects, the functional roles of endogenous ligands for $CB_1$ and $CB_2$ receptors remain poorly defined [Mechoulam et al., *Prog. Med., Chem.*, 35:199-243 (1998)]. Early observations suggest a potent neuromodulatory role for these endocannabinoids [Cravatt et al., *Science*, 268:1506-9 (1995); Mendelson et al., *Neuroreport*, 10:3237-9 (1999); Santucci et al., *Life Sci*, 58: L103-10 (1996); Varga et al., *Eur. J. Pharmacol*, 278:279-83 (1995); Varga et al., *Hypertension*, 28:682-6 (1996)]. Cannabinoid receptors interact with opiate, GABA, dopamine, glutamate, and serotonin systems [Di Marzo et al., *Trends Neurosci*, 21:521-8 (1998)], all of which influence level of arousal and autonomic regulation, both behaviors of fundamental importance.

Of particular interest is the fact that activation of serotonin receptors within the peripheral nervous system can lead to significant autonomic perturbations, especially during sleep. For example, stimulating peripheral 5-$HT_3$ receptors exacerbates apnea expression specifically during rapid eye movement (REM) sleep [Carley and Radulovacki, *Chest*, 115: 1397-401 (1999)]. By altering serotonin receptor function, endocannabinoids also may impact sleep/wake and autonomic behaviors, but the serotonin/cannabinoid interaction appears to be receptor subtype specific and the published findings are not fully consistent.

More specifically, some studies indicate that cannabinoids enhance responses to serotonin. For example, Cheer et al. [*Neuropharmacol.*, 38;533 (1999)] found that certain 5-$HT_2$ receptor-induced motor behaviors in rats were enhanced by pretreatment with either oleamide or HU210, a $CB_1$, receptor agonist. Conversely, Kimura et al. [*Biol. Pharm. Bull.*, 21:224 (1998)] demonstrated that anandamide, an endocannabinoid, decreased 5-HT receptor binding in synaptic membranes in vitro, and Fan [*J. Neurophysiol.*, 73:907 (1995)] reported that several $CB_1$ receptor agonists, including anandamide, inhibited 5-HT$_3$ receptor-mediated currents in rat nodose ganglion cells in a dose dependent manner.

Significant autonomic disturbances may occur in any stage of sleep. A particularly dramatic example is transient cessation of respiration, or apnea. When apnea occurs with sufficient frequency during sleep, significant behavioral and clinical morbidity can result. Our data show that the exogenous cannabinoid (CB$_1$) receptor agonist $\Delta^9$THC and the endogenous cannabimimetic fatty acid amide oleamide each stabilize respiratory pattern during all sleep stages by producing dose-dependent reductions in apnea expression. This observation suggests an important role for endocannabinoids in maintaining autonomic stability during sleep. We present additional findings to argue that the effects on respiration may result from inhibitory coupling between cannabinoids and serotonin receptors in the peripheral nervous system.

Given the foregoing, experiments were conducted to test the effects of cannabimimetics in freely moving animals in order to assess for inhibition of expression of spontaneous apneas during NREM and REM sleep Example 1 describes the preparation of the animals for treatment with the cannabimimetics and subsequent physiological recording and testing.

Example 2 describes the methods for the physiological recording of treatment and control animals and results obtained from administration of cannabimimetics.

Example 3 describes methods for the prevention or amelioration of sleep-related breathing disorders via administration of cannabimimetics.

The following examples are illustrative of aspects of the present invention but are not to be construed as limiting.

EXAMPLE 1

Preparation of Animals for Physiological Testing and Recording

Sprague-Dawley rats exhibit respiratory disturbance n the form of spontaneous apnea during all sleep stages, but with the greatest frequency during REM sleep [Carley and Radulovacki, in *Rapid Eye Movement Sleep*, B. N. Mallick, S. Inoue, Eds; Narosa Publishing, New Delhi, 1999; pp. 286-300]. These recoding and data analysis methods have been described in detail elsewhere [Carley and Radulovacki (*Chest.*, 115: 1397 (1999)].

Adult, male Sprague-Dawley rats (Sasco-King, Wilmington, Mass.; 11 per test group; 300 g) were maintained on a 12-hour light (08:00-20:00 hour)/12-hour dark (20:00-08:00 hour) cycle for one week, housed in individual cages and given ad libitum access to food and water. Following the one week of acclimatization, animals were subjected to the following surgical procedures.

Acclimatized animals were anesthetized for the implantation of cortical electrodes for electroencephalogram (EEG) recording and neck muscle electrodes for electromyogram (EMG) recording using a mixture of ketamine (Vedco, Inc., St. Joseph, Mo.; 80 mg/ml) and xylazine (Vedco, Inc., St. Joseph, Mo.; 5 mg/ml; 4:1, volume/volume) at a volume of 1 ml/kg body weight. The surface of the skull was exposed surgically and cleaned with a 20% solution of hydrogen peroxide followed by a solution of 95% isopropyl alcohol. Next, a dental preparation of sodium fluoride (Flura-GEL®, Saslow Dental, Mt. Prospect, Ill.) was applied to harden the skull above the parietal cortex and allowed to remain in place for 5 minutes. The fluoride mixture was then removed from the skull above the parietal cortex. The EEG electrodes consisting of four stainless steel machine screws, having leads attached thereto, were threaded into the skull to rest on the dura over the parietal cortex. A thin layer of Justi® resin cement (Saslow Dental, Mt. Prospect, Ill.) was applied to cover the screw heads (of screws implanted in the skull) and surrounding skull to further promote the adhesion of the implant. EMG electrodes consisting of two ball-shaped wires were inserted into the bilateral neck musculature. All leads (i.e., EEG and EMG leads) were soldered to a miniature connector (39F1401, Newark Electronics, Chicago, Ill.). Lastly, the entire assembly was fixed to the skull with dental cement.

After surgery, all animals were allowed to recover for one week before being subjected to another surgery that involved implantation of a radiotelemetry transmitter (TA11-PXT, Data Sciences International, St. Paul, Minn.) for monitoring blood pressure (BP) and heart period (HP), estimated as pulse interval. After the animals were anesthetized (as described above), the hair from the subxiphoid space to the pelvis was removed. The entire area was scrubbed with iodine and rinsed with alcohol and saline. A 4-6 cm midline abdominal incision was made to allow good visualization of the area from the bifurcation of the aorta to the renal arteries. A retractor was used to expose the contents of the abdomen and the intestine was held back using saline moistened gauze sponges. The aorta was dissected from the surrounding fat and connective tissues using sterile cotton applicators. A 3-0 silk suture was placed beneath the aorta and traction was applied to the suture to restrict the blood flow. Then the implant (TA11-PXT) was held by forceps while the aorta was punctured just cranial to the bifurcation using a 21-gauge needle bent at the beveled end. The tip of the catheter was inserted under the needle using the needle as a guide until the thin-walled BP sensor section was within the vessel. Finally, one drop of tissue adhesive (Vetbond®, 3M, Minneapolis, Minn.) was applied to the puncture site and covered with a small square of cellulose fiber (approximately 5 mm$^2$) so as to seal the puncture after catheter insertion. The radio implant was attached to the abdominal wall by 3-0 silk suture, and the incision was closed in layers. After the second surgery, animals were again allowed a one week recovery period prior to administration of a cannabinoid receptor agonist or a cannabimimetic and subsequent physiological recording.

EXAMPLE 2

Physiological Recording and Suppression of Apneas $\Delta^9$THC (dronabinol, Roxane Laboratories, Columbus, Ohio) was dissolved in DMSO: oleamide (ICN Biomedicals, Aurora, Ohio) was suspended in peanut oil with sonnication for 20 minutes; and serotonin was dissolved in saline. The study was a fully nested, repeated measures crossover design, such that each animal received each of 12 intraperitoneal injections (1 ml/kg) exactly one time: vehicle alone (saline, DMSO, or peanut oil); $\Delta^9$THC alone (0.1, 1.0, or 10.0 mg/kg); oleamide alone (0.1, 1.0, or 10.0 mg/kg); serotonin alone (0.79 mg/kg); or combination injection (0.1 mg/kg $\Delta^9$THC followed, after 15 minutes, by 0.79 mg/kg serotonin or 0.1 mg/kg oleamide followed by 0.79 mg/kg serotonin). Each injection was made 15 minutes prior to polygraphic recording for 6 hours (10:00-16:00). Successive recordings for an individual animal were separated by at least three days and the treatments were given in random order.

Respiration was recorded by placing each animal, unrestrained, inside a single chamber plethysmograph (PLYUN1R/U; Buxco Electronics, Sharon, Conn.; dimension 6 in.×10 in.×6 in.) ventilated with a bias flow of fresh room air at a rate of 2 L/min. A cable plugged onto the animal's connector and passed through a sealed port was used to carry the bioelectrical activity from the head implant. Respiration, blood pressure, EEG activity, and EMG activity were displayed on a video monitor and simultaneously digitized 100 times per second and stored on computer disk (Experimenter's Workbench; Datawave Technologies, Longmont, Colo.).

Sleep and waking states were assessed using the biparietal EEG and nuchal EMG signals on 10-second epochs as described by Bennington et al. [*Sleep* 17:28-36 (1994)]. This software discriminated wakefulness (W) as a high frequency low amplitude EEG with a concomitant high EMG tone, NREM sleep by increased spindle and theta activity together with decreased EMG tone, and REM sleep by a low ratio of a delta to theta activity and an absence of EMG tone. Sleep efficiency was measured as the percentage of total recorded epochs staged as NREM or REM sleep.

The bias flow of room air (2 l/min) was more than one order of magnitude greater than the alveolar ventilation of the rat, ensuring that no rebreathing occurred. Thermal fluctuations associated with tidal respiration induced changes in plethysmograph pressure proportional to tidal volume. Plethysmograph pressure was monitored using a Validyne DP45-14 differential pressure transducer (±2 cm H20). Prior to each experimental study, the plethysmograph was calibrated for tidal volume using the method described by Epstein et al. (*J. Appl. Physiol.*, 49, 1107 (1980)). An adaptive threshold algorithm (Datawave Systems, Longmont, Colo.) was used to measure the duration and tidal amplitude of each breath in each recording. From these values, instantaneous respiratory rate (RR) and minute ventilation (MV) were computed on a breath by breath basis. Respiratory variability was assessed by calculating the standard deviations of RR and MV for each 10 second recording epoch. These standard deviations were then averaged separately for each sleep/wake state.

An accepted physiological animal model [rat; Monti, et al., *Pharmacol. Biochem. Behav.*, 51:125-131; (1995)] of sleep apnea was used to assess the effects of a cannabinoid receptor agonist activity and/or agents having cannabimimetic activity. More specifically, sleep apneas, defined as cessation of respiratory effort for at least 2.5 seconds, were scored for each recording session and were associated with the stage in which they occurred: NREM or REM sleep. The duration requirement of 2.5 seconds represented at least 2 "missed" breaths, which is therefore analogous to a 10 second apnea duration requirement in humans, which also reflects 2-3 missed breaths. The events detected represent central apneas because decreased ventilation associated with obstructed or occluded airways would generate an increased plethysmographic signal, rather than a pause. An apnea index (AI), defined as apneas per hour in a stage was separately determined for NREM and REM sleep. The effects of sleep stage (NREM vs. REM) and injection (control vs. test compounds) were tested using ANOVA with repeated measures. Multiple comparisons were controlled using Fisher's protected least significant difference (PLSD). In addition, the timing and volume of each breath were scored by automatic analysis (Experimenters' Workbench; Datawave Technologies, Longmont, Colo.). For each animal the mean respiratory rate (RR) and minute ventilation (MV) was computed for W throughout the 6 hour control recording and used as a baseline to normalize respiration during sleep and during test compound administration in that animal. One way ANOVA was also performed by non-parametric (Kruskal-Wallis) analysis. Conclusions using parametric and non-parametric ANOVA were identical in all cases.

Similar software (Experimenters' Workbench; Datawave Technologies, Longmont, Colo.) was employed to analyze the blood pressure waveform; for each beat of each recording, systolic (SBP) and diastolic (DBP) blood pressures and pulse interval were measured. The pulse interval provided a beat by beat estimate of HP. Mean BP (MBP) was estimated according to the weighted average of SBP and DBP for each beat: MBP=DBP+(SBP−DBP)/3. The parameters for each beat were also classified according to the sleep/wake state and recording hour during which they occurred.

Extreme variations in respiratory pattern, as represented by apneas, were reduced by both test compounds. $\Delta^9$THC strongly suppressed spontaneous apnea during all sleep stages; (F=2.68; p=0.04), but this effect was not time-dependent (F=0.91, p=0.57 for NREM; F=0.71, p=0.82 for REM) during the 6-hour recording period. Post hoc comparisons (controlled by Fisher's protected least significance difference) demonstrated that $\Delta^9$THC doses of 1.0 and 10.0 mg/kg reduced the frequency of apneas during NREM sleep (p=0.03 for each), whereas only the 10.0 mg/kg dose produced a significant decrease during REM sleep (p=0.03).

Figure 1A:
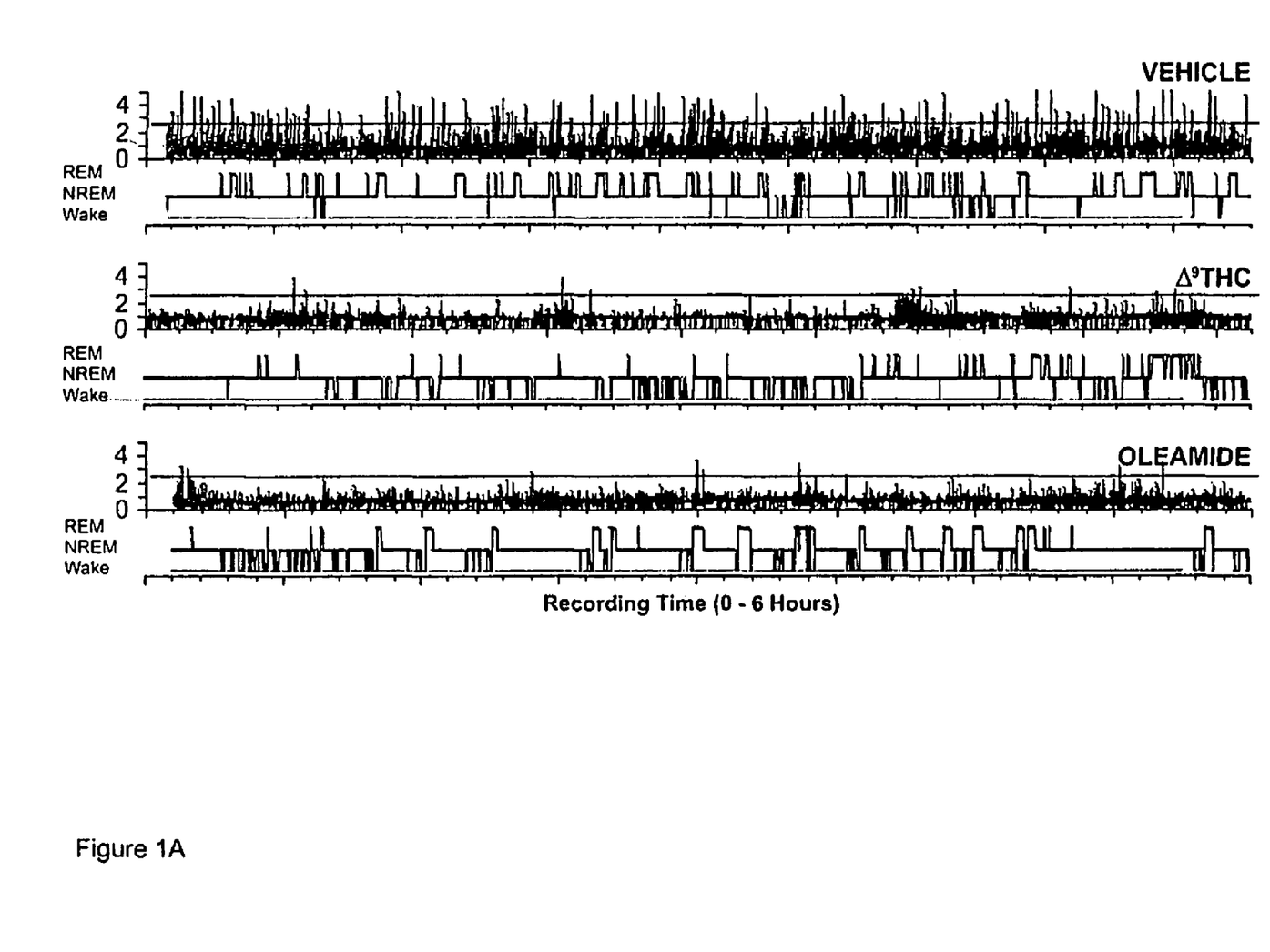
FIG. 1A shows the relationship between breath duration and sleep/wake states in typical 6-hour recordings made after injection of vehicle (upper panel), 10.0 mg/kg of $\Delta^9$THC (middle panel), or 10.0 mg/kg of oleamide (lower panel). Within each panel, the lower tracing depicts transitions among Wake, NREM sleep, and REM sleep as a step function. The upper tracing presents the duration of each of the approximately 30,000 breaths during the recording. Whenever breath duration exceeded 2.5 seconds (above the horizontal threshold line) an apnea was scored. It can be observed during vehicle (control) recordings that respiratory rate was quite variable, that apneas occurred intermittently throughout the recording, and REM sleep often was associated with flurries of apnea. In contrast, injection of either $\Delta^9$THC or oleamide produced a clear reduction in breaths with durations exceeding 1.5 seconds.
Figure 1B:
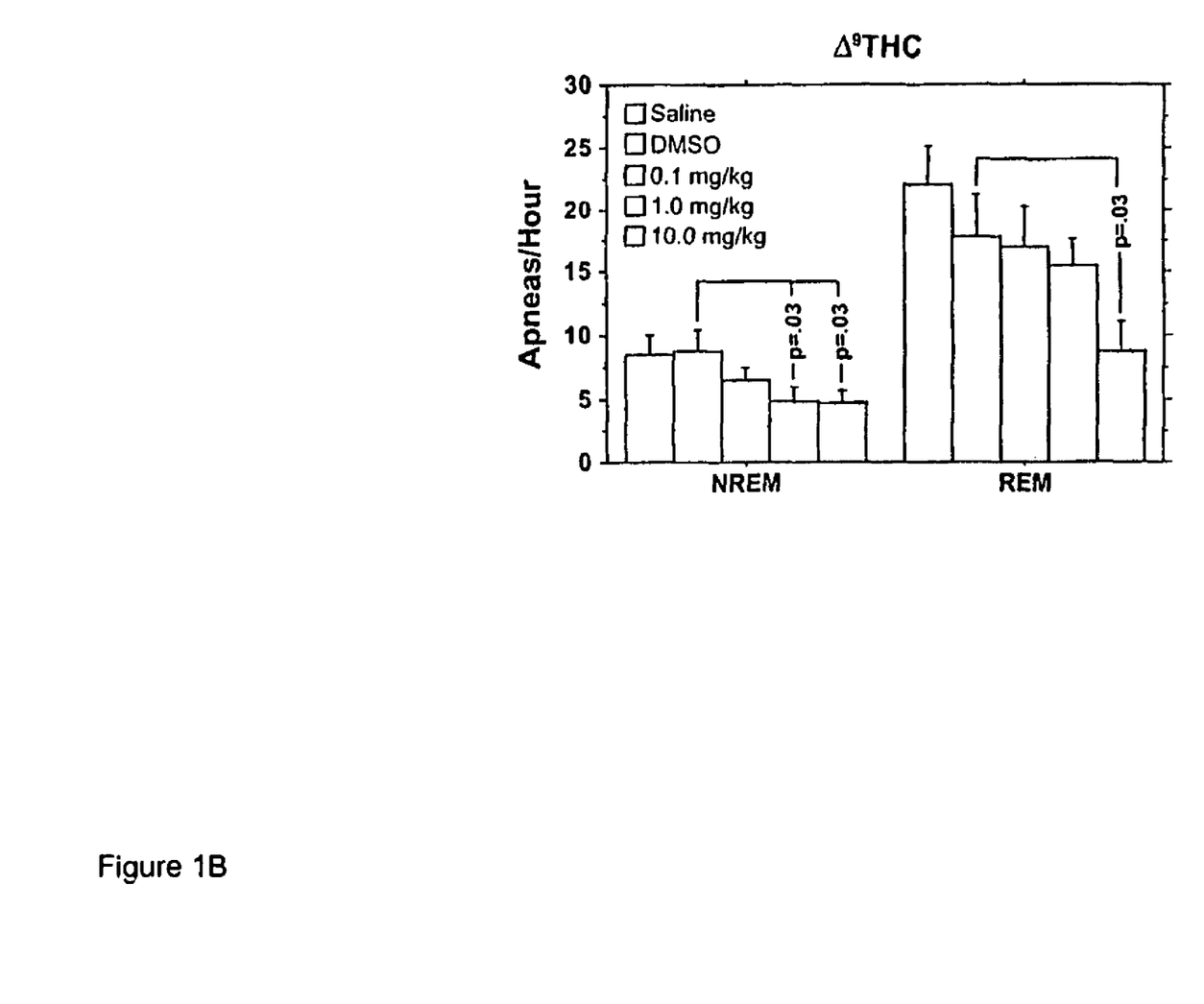
FIG. 1B sets forth group mean data illustrating the dose-dependent suppression of spontaneous apnea by $\Delta^9$THC during NREM (left column) and REM (right column) sleep. The ordinate represents apneas per hour of NREM sleep (left) or per hour of REM sleep (right). Injections are coded according to the inset legend. With respect to vehicle (DMSO), dose dependent reductions in apnea expression were observed as labeled.
Figure 1C:
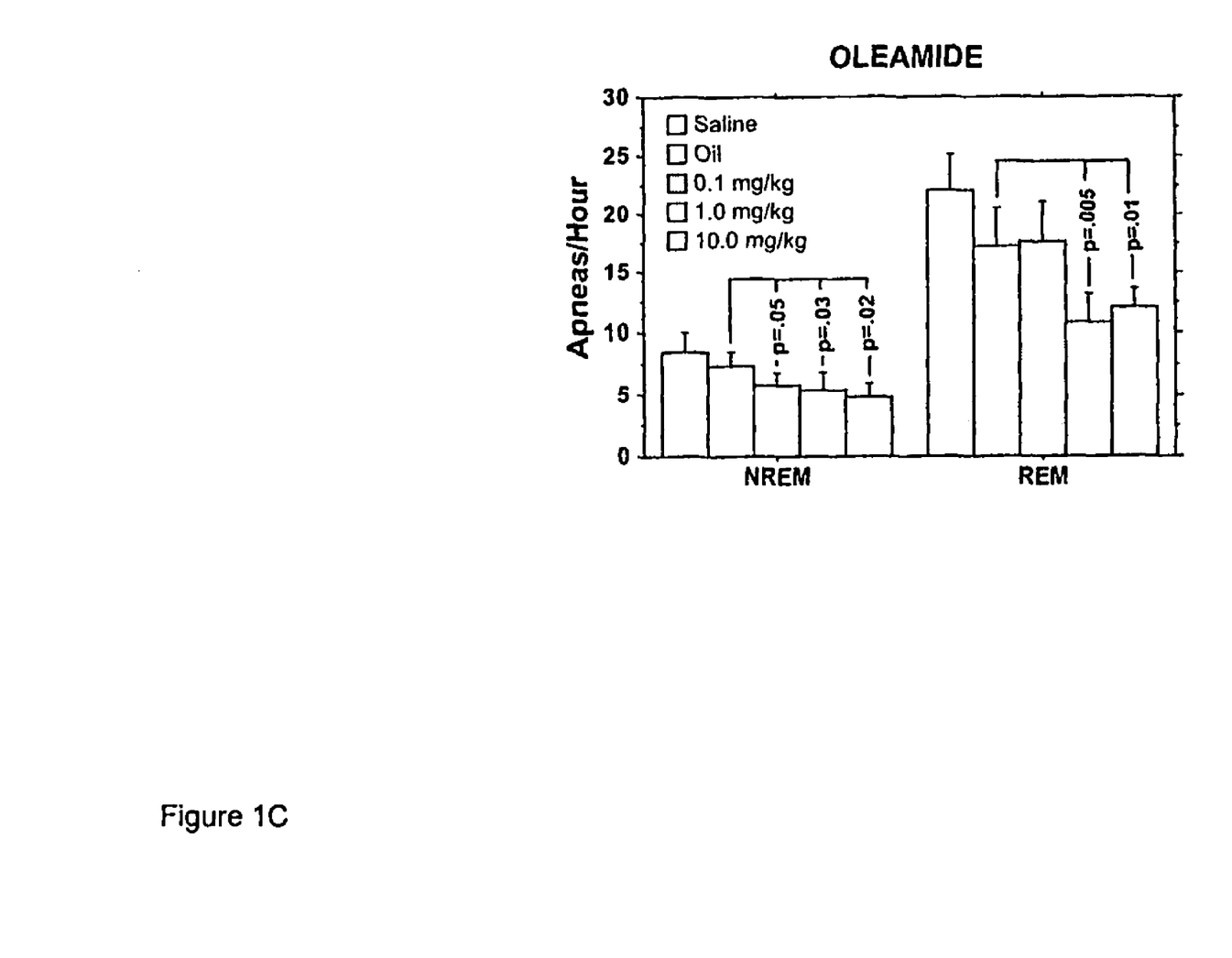
FIG. 1C shows group mean data illustrating impact of oleamide on apnea expression presented in the format of panel B. Again, dose dependent apnea suppression was observed as labeled.

Oleamide, an endogenous fatty acid amide, mimicked the apnea suppression produced by the exogenous $CB_1$ receptor agonist $\Delta^9$THC (FIG. 1). With respect to the vehicle, oleamide suppressed apnea expression during NREM sleep at all three doses and during REM sleep at the two higher doses (p<0.05 for each). At the highest-dose, the degree of apnea suppression was equivalent for $\Delta^9$THC and oleamide. Oleamide's ability to suppress apnea persisted throughout the 6 hour recording interval (F=1.24, p=0.23 for NREM; F=0.72, p=0.80 for REM).

Figure 2A:
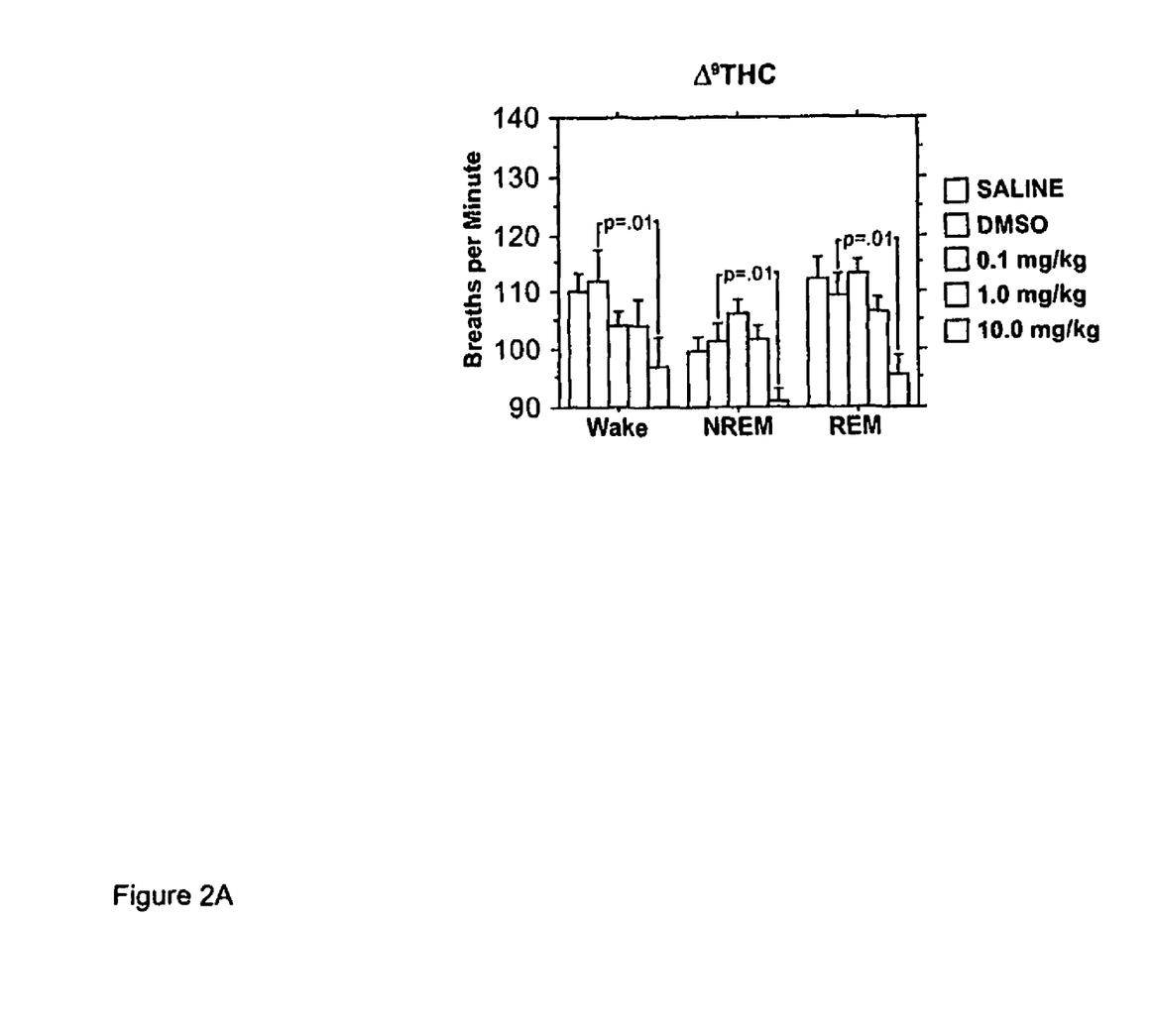
Figure 2B:
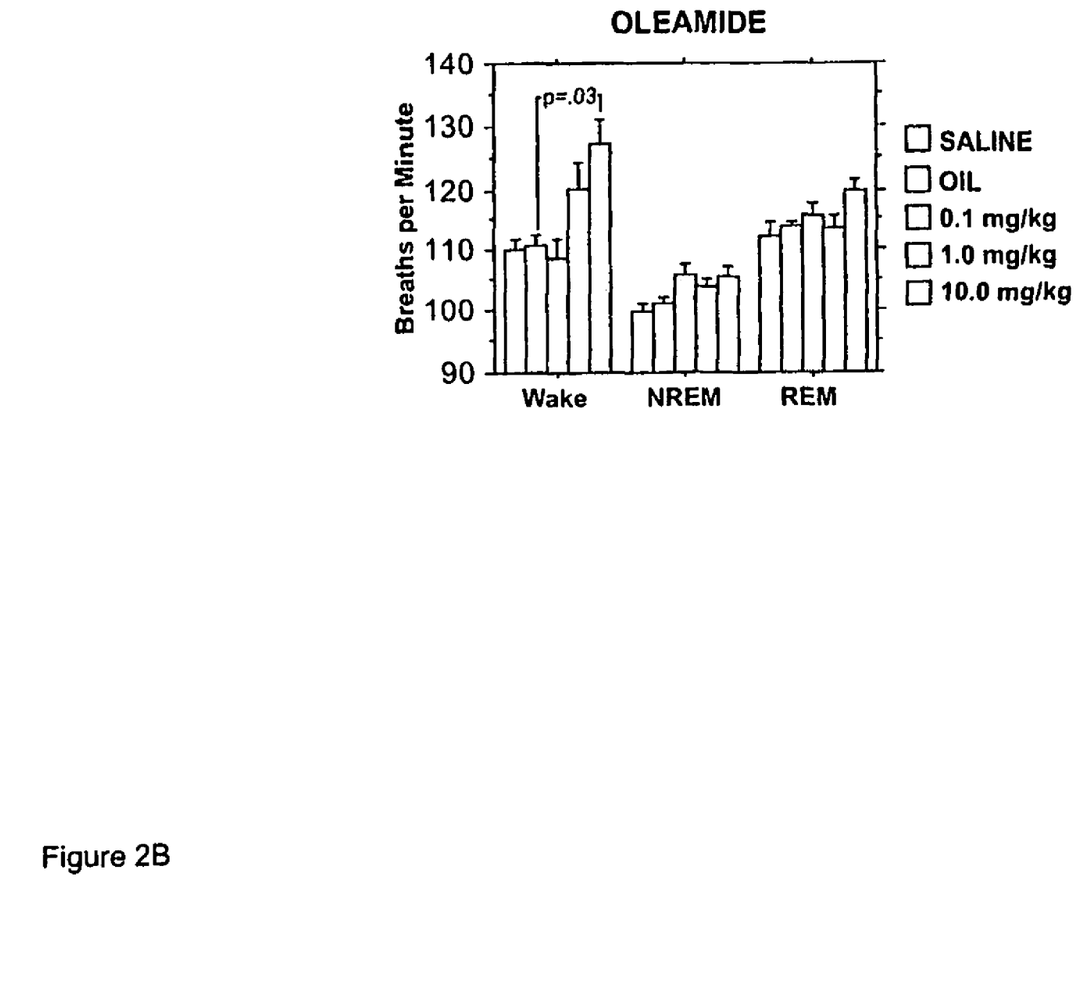
FIG. 2B shows group mean data (n=11) for impact of oleamide on average RR throughout 6-hour recordings. RR tended to increase after administration of 10.0 mg/kg oleamide. Again, RR was lowest during NREM sleep and was unaffected by time during the recording.

$\Delta^9$THC and oleamide each altered average respiratory rate (RR), but with opposite effects (FIG. 2). $\Delta^9$THC evoked a dose dependent reduction in RR during all sleep/wake states (F=4.67, p=0.003). Conversely, oleamide produced dose dependent elevation of RR, an effect which achieved statistical significance only during wakefulness (p=0.03 for 10.0 mg/kg vs. vehicle). Equivalent effects were observed for respiratory minute ventilation. Average tidall volume was unaffected by any injection. RR also displayed the expected decrease during non rapid eye movement (NREM) sleep (F=25.8, p<0.0001 for effect of sleep; F=1.49, p=0.17 for interaction between sleep state and injection type), an effect which was evident throughout the recording interval (F=0.98, p=0.52 for interaction between sleep state and recording hour—see FIG. 2).

Figure 3:
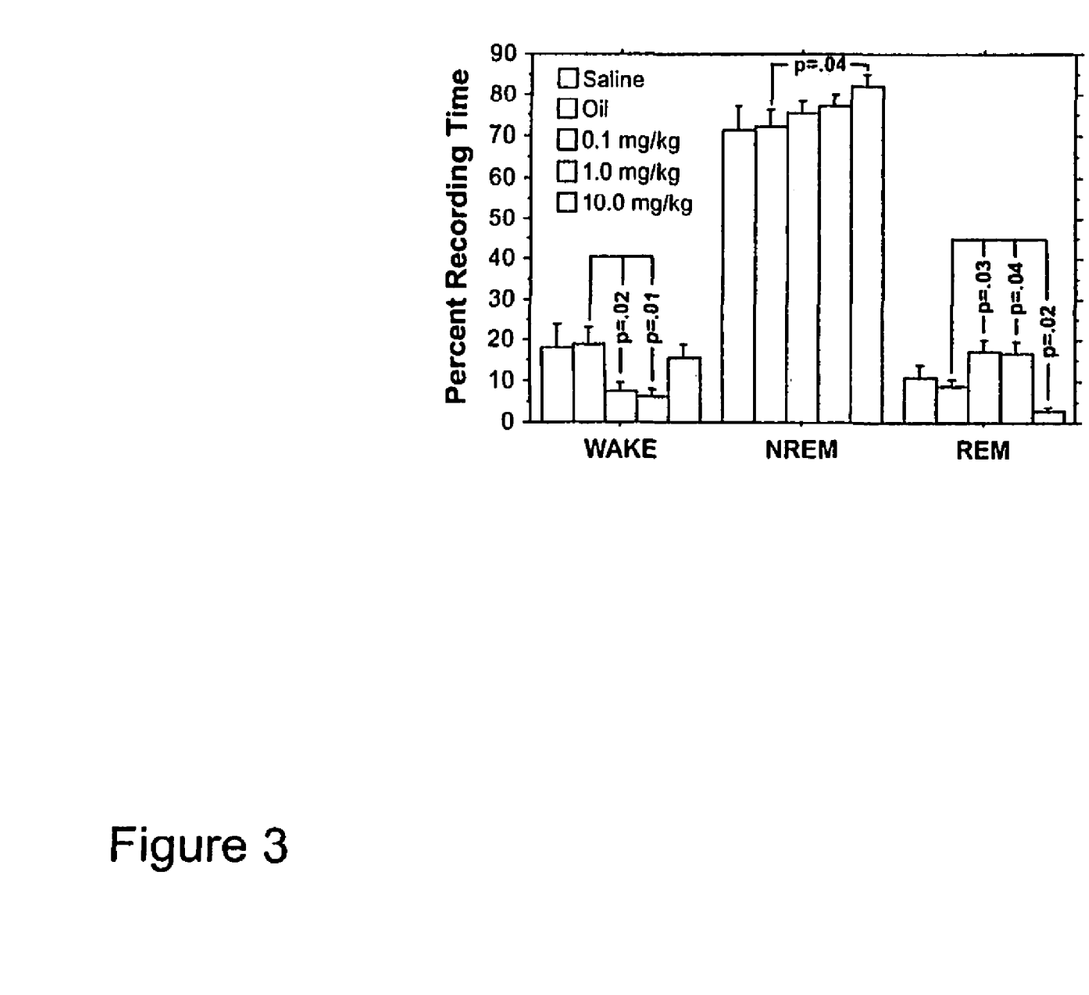

Oleamide produced a significant alteration of sleep/wake architecture (FIG. 3). Throughout the 6 hour recording (F=1.38, p=0.14 for interaction of time and dose), administration of 0.1 of 1.0 mg/kg oleamide produced increased REM sleep with decreased wakefulness, whereas the 10.0 mg/kg dose resulted in increased NREM sleep with decreased REM sleep. These hypnotic properties of oleamide confirm similar previous observations (4, 14). The only change in sleep architecture produced by $\Delta^9$THC was a decrease in REM sleep expression at the highest dose tested (−66%, p=0.0002; data not shown).

Figure 4:
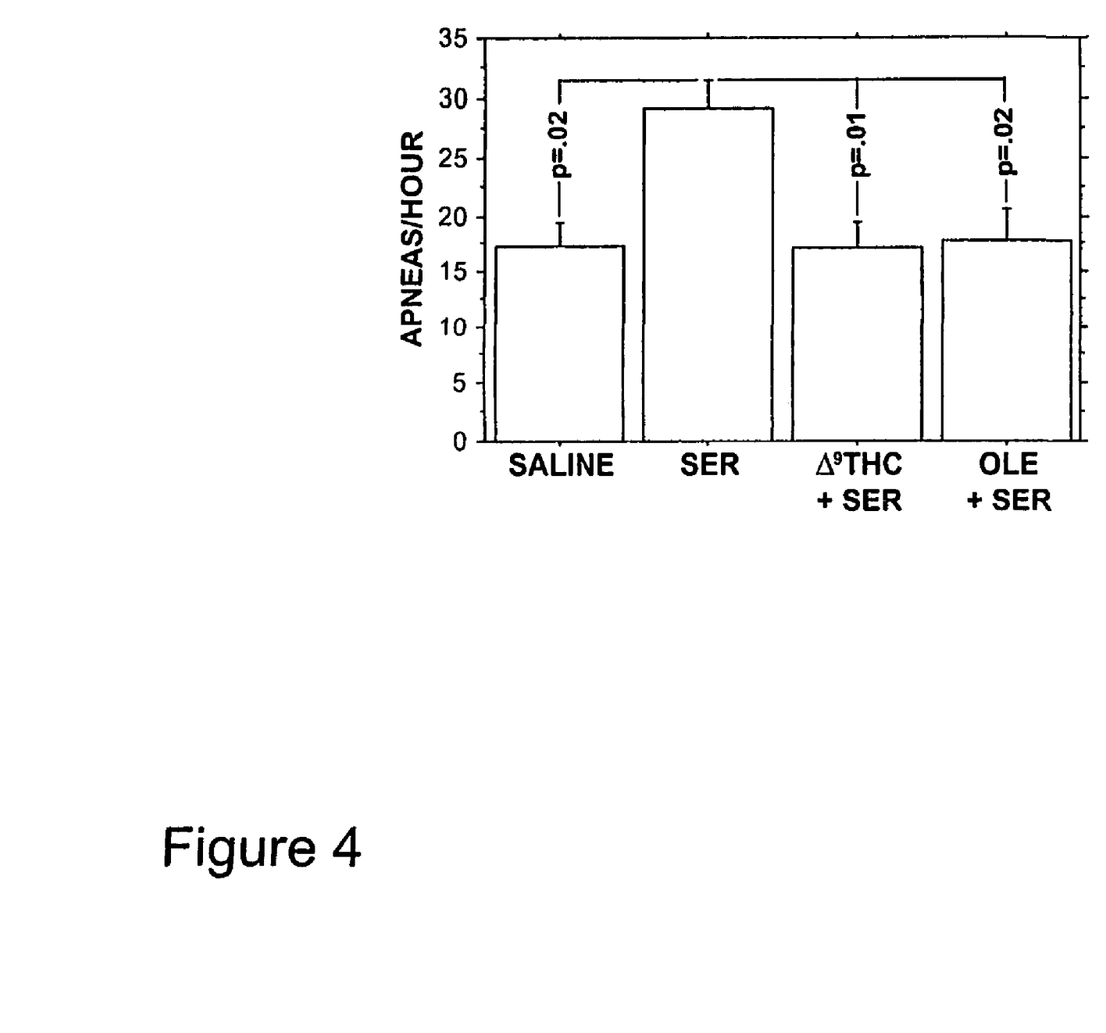
FIG. 4. shows group mean data for 6-hour recordings demonstrating the frequency of apnea during REM sleep following intraperitoneal injection of vehicle (saline), serotonin (0.79 mg/kg, SER) alone, or serotonin following pretreatment by $\Delta^9$THC (0.1 mg/kg, SER+$\Delta^9$THC), or oleamide (0.1 mg/kg, SER+OLE). Serotonin produced a significant increase in REM sleep-apnea; an effect which was completely blocked by pretreatment with either $\Delta^9$THC or oleamide. Transient but physiologically significant perturbations of autonomic homeostasis can be observed during all levels of sleep, but with the greatest frequency and intensity during REM sleep.

As previously demonstrated, serotonin produced a significant increase in the frequency of apnea during REM sleep (FIG. 4). This peripheral effect of serotonin was completely blocked by pretreatment with 0.1 mg/kg of either $\Delta^9$THC or oleamide. At this dose, neither $\Delta^9$THC nor oleamide had any effect on apnea expression during REM sleep when administered along (FIG. 1).

Transient but physiologically significant perturbations of autonomic homeostasis can be observed during all levels of sleep, but with the greatest frequency and intensity during REM sleep. A particularly dramatic example is transient cessation of respiration, or apnea. When apnea occurs with sufficient frequency during sleep, significant behavioral and clinical morbidity can result. Our data show that the $CB_1$ receptor agonist $\Delta^9THC$ stabilizes respiratory pattern during all sleep stages by producing a dose-dependent reduction of apnea expression.

$CB_1$ receptors have been demonstrated in peripheral neurons, albeit at lower densities than in the central nervous system. The function of these receptors, however, has not been well demonstrated. The ability of $\Delta^9THC$ to completely block serotonin-induced apnea exacerbation, at a dose that exerted no independent effect on any behavior measured, argues that $CB_1$ receptors in the peripheral nervous system exert a significant influence on serotonin receptor signaling. The possibility that endogenous serotonin may act at receptors in the peripheral nervous system to promote autonomic perturbations such as apnea (9) is consistent with our finding that sufficient doses of $\Delta^9THC$ alone can suppress spontaneous apnea (FIG. 2).

The endocannabinoid oleamide completely mimicked the ability of $\Delta^9THC$ to suppress spontaneous and serotonin-induced apnea (FIGS. 2 and 3). Although not conclusive, this parallelism suggests that the actions of oleamide and $\Delta^9THC$ are convergent at some point in the signaling cascade. It is unlikely that these effects of oleamide are directly mediated via cannabinoid receptors, because oleamide does not appear to bind with high affinity to $CB_1$ or $CB_2$ receptors. Still, oleamide exerts cannabimimetic actions that could be explained at least in part by entourage effects. It is likely that oleamide and anandamide, an endogenous $CB_1$ agonist, have common as well as distinct pathways of action. The increased stability of respiratory pattern produced by $\Delta^9THC$ and oleamide does not appear to be a nonspecific by-product of respiratory stimulation, because the two compounds exerted opposite effects on average respiratory rate and minute ventilation (FIG. 1).

Our data has provide a rationale for exploring use of cannabimimetic drugs in the treatment or sleep related breathing disorders. In this regard, endocannabinoids that can promote deep sleep, such as oleamide, may have advantages over agents which have no effect on, or interfere with sleep.

EXAMPLE 3

Apnea Suppression

In view of the foregoing observations, sleep related breathing disorders (sleep apnea syndrome, apnea of infancy, Cheyne-Stokes respiration, sleep-related hypoventilation syndromes) may also be effectively suppressed or prevented via administration of cannabimimetic agents or combinations of cannabimimetic agents.

Those of skill in the art will recognize that cannabimimetic agents may be selected from (but are not limited to) cannabinoid receptor agonists such as $\Delta^9THC$, WIN55212-2, CP55940, CP54939, HU308, HU211 (dexanabinol), nabilone, cannabinol, 11-hydroxcannabinol, O-1057, levonantradol, anandamide, R1-methanandamide, and 2-arachidonylglycerol; endocannabimimetics such as oleamide and palmitoylethanolamide and synthetic derivatives related thereto, and agents that prolong the action of endocannabimimetics, such as AM404 (endocannabinoid transport inhibitor) and 2-octyl-gamma-bromoacetoacetate, ibuprofen, ketoralac, and flurdiprofen (all fatty acid amide hydrolase inhibitors, which enzyme breaks down endocannabinoids).

An individual diagnosed with a sleep-related breathing disorder is administered either a composition or agent having any of the foregoing pharmacological profiles in an amount effective to prevent or suppress such disorders. The specific dose may be calculated according to such factors as body weight or body surface. Further refinement of the calculations necessary to determine the appropriate dosage for treatment of sleep-related breathing disorders is routinely made by those of ordinary skill in the art without undue experimentation. Appropriate dosages may be ascertained through use of established assays for determining dosages. Routes of administration for the foregoing methods may be by any systemic means including oral, intraperitoneal, subcutaneous, intravenous, intramuscular, transdermal, or by other routes of administration. Osmotic mini-pumps and timed-released pellets or other depot forms of administration may also be used.

Finally, those of skill in the art will recognize that with respect to the compounds discussed above, such compounds may contain a center of chirality. Thus such agents may exist as different enantiomers of enantiomeric mixtures. Use of any one enantiomer alone or contained within an enantiomeric mixture with one or more stereoisomers is contemplated by the present invention.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements. All literature cited herein is incorporated by reference.

What is claimed is:

1. A method of ameliorating sleep apnea comprising administering to a patient in need thereof an effective amount 9-tetrahydrocannabinol or oleamide.

2. The method of claim 1 wherein the patient experiences a reduced number of periodic cessations of breathing during sleep.

3. The method of claim 1 wherein the patient experiences a reduced number of recurrent episodes of nocturnal asphyxia during sleep.

4. The method of claim 1 wherein the patient experiences a reduced number of arousals from sleep.

* * * * *